United States Patent
Roundhill

(12)
(10) Patent No.: US 6,516,215 B1
(45) Date of Patent: Feb. 4, 2003

(54) DIAGNOSTIC ULTRASOUND IMAGING SYSTEM HAVING DISPLAY CONFIGURED TO OPTIMALLY DISPLAY ULTRASOUND IMAGES

(75) Inventor: David N. Roundhill, Woodinville, WA (US)

(73) Assignee: ATL Ultrasound, Inc., Bothell, WA (US)

( * ) Notice: Subject to any disclaimer, the term of this patent is extended or adjusted under 35 U.S.C. 154(b) by 52 days.

(21) Appl. No.: 09/717,907

(22) Filed: Nov. 20, 2000

(51) Int. Cl.⁷ .................................................. A61B 8/00
(52) U.S. Cl. ....................................................... 600/432
(58) Field of Search .................................. 600/437, 459, 600/460, 454, 451

(56) References Cited

U.S. PATENT DOCUMENTS

| | | | | |
|---|---|---|---|---|
| 5,782,766 A | * | 7/1998 | Weng et al. ................. | 128/916 |
| 6,007,490 A | * | 12/1999 | Pawluskiewicz ............ | 600/459 |
| 6,099,474 A | * | 8/2000 | Solek .......................... | 600/440 |
| 6,142,945 A | * | 11/2000 | Sakamoto et al. .......... | 600/459 |
| 6,213,944 B1 | * | 4/2001 | Miller et al. ................ | 600/437 |

* cited by examiner

Primary Examiner—Francis J. Jaworski
Assistant Examiner—Maulin Patel
(74) Attorney, Agent, or Firm—Dorsey & Whitney LLP

(57) ABSTRACT

A diagnostic ultrasound imaging system includes a display monitor having a viewing screen with an aspect ratio substantially wider than 4:3. The wide aspect ratio screen is able to display horizontally elongated images typically obtained in ultrasound imaging using a greater percentage of the viewing screen compared to display monitors used in prior art ultrasound imaging systems. As a result, the images can be seen with greater size and resolution without cutting off portions of the images. The display monitor is preferably rotatable 90 degrees to provide a viewing screen having an aspect ratio substantially narrower than display monitors used in prior art ultrasound imaging systems, thereby providing a viewing screen that is better able to show deep images.

29 Claims, 6 Drawing Sheets

DIAGNOSTIC ULTRASOUND IMAGING SYSTEM HAVING DISPLAY CONFIGURED TO OPTIMALLY DISPLAY ULTRASOUND IMAGES

TECHNICAL FIELD

This invention relates to diagnostic ultrasound systems, and more particularly, to displays for diagnostic ultrasound systems.

BACKGROUND OF THE INVENTION

Diagnostic ultrasound systems are commonly used to image a wide variety of organs and tissues within the human body. A typical diagnostic ultrasound imaging system 10 is shown in FIG. 1. The diagnostic ultrasound imaging system 10 includes an ultrasound transducer 14 that is adapted to be placed in contact with a portion of a body that is to be imaged. The transducer 14 is coupled to a system chassis 16 by a cable 18. The system chassis 16, which is mounted on a cart 20, includes a keyboard 24 by which data may be entered into a processor (not shown) that is included in the system chassis 16. A display monitor 30 having a viewing screen 34 is placed on an upper surface of the system chassis 16. As is typical, the viewing screen 34 has the same 4:3 aspect ratio as conventional television and computer monitors.

While displays having a 4:3 aspect ratio are suitable for performing many imaging tasks, they are far from ideal for many imaging applications. One example of an imaging application that is not well suited for display on a monitor having a 4:3 aspect ratio is a panoramic image. In panoramic imaging, the transducer 14 is scanned along the surface of a portion of the body, such as an arm. FIG. 2 shows a panoramic image 40 of an arm displayed on the viewing screen 34 of an ultrasound imaging system. Because panoramic images are created by scanning the transducer 14 along a path, panoramic images are typically horizontally elongated, as is the panoramic image 40 shown in FIG. 2. As shown in FIG. 2, most of the screen 32 is blank, and the anatomical features in the image 40 are quite small. Furthermore, the number of pixels used to display the image, and hence its resolution, may be significantly limited. The anatomical features could be shown in greater detail and with greater resolution by increasing the scale of the image 40, but doing so would cause the end portion of the image 40 to be outside the viewing area of the screen 32. The problem with displaying panoramic images using conventional display monitors is, therefore, not only the size of the anatomical details in the image, but also the resolution at which those details may be displayed. Thus, conventional display monitors, such as those having an aspect ratio of 4:3, do not provide optimum results for panoramic imaging.

Another imaging application that produces an image having an aspect ratio similar to panoramic imaging is shallow depth scanning, which is also known as peripheral scanning. The scan depth of such images is often very shallow so that the horizontal dimension of the image is significantly greater than the vertical dimension. As with panoramic images, it can be difficult to see fine detail in images produced by peripheral scanning without increasing the scale of the image. However, increasing the scale of the image may cut off a portion of the image. It is therefore not possible to see the entire image and still display the image with enough resolution and size to make it possible to clearly view fine anatomical features.

Another example where conventional display monitors used in ultrasound imaging systems provide limited performance is in the side-by-side presentation of multiple images. With reference to FIG. 3, in side-by-side imaging, the viewing screen 34 is divided into two areas, and an image is displayed on each area of the screen 34. Since the viewing screen has an aspect ratio of 4:3, each of the areas on which an image is displayed has an aspect ratio of 2:3. As shown in FIG. 3, an ultrasound image 50 is displayed on the left hand side of the viewing screen 34, and text or a second image 52 is displayed on the right hand side of the screen. The image 52 may be, for example, another ultrasound image or a magnetic resonance image, an x-ray, a nuclear image, an image obtained by CT scanning, or a graphical image, to name a few examples. The display of the ultrasound image 50 with an aspect ratio of 2:3 only serves to exacerbate the problems described above with displaying certain types of ultrasound images.

Another application of ultrasound imaging that provides less than optimum performance because of the limitations of conventional display monitors is spectral Doppler scanning. In spectral Doppler scanning, a portion of the viewing screen 34 is used to display a two-dimensional ultrasound image that generally includes a blood vessel. Another portion of the viewing screen 34 is used to display a graph in which the velocity of blood in the vessel being scanned is displayed on the "Y" axis as a function of time, which is displayed along the "X" axis in scrolling fashion. A typical example of the viewing screen 34 when the ultrasound imaging system 10 is being used for Doppler scanning is shown in FIG. 4. As shown in FIG. 4, an ultrasound image 60 is typically displayed on the upper portion of the viewing screen 34 and a velocity graph 62 is displayed on the lower portion of the viewing screen 34. Although the wider aspect ratio of the ultrasound image 60 can be advantageous for reasons discussed herein, the presence of the velocity graph 62 prevents the full height of the viewing screen 34 from being used to display the ultrasound image 60. It would be preferable to be able to display the ultrasound image 60 using the full height of the viewing screen 34 and still be able to display the velocity graph 62.

Still another example of an imaging application for which conventional display monitors are not well suited for display is deep imaging. In deep imaging, a relatively narrow image is obtained fairly deep into the body. An example of an image 70 obtained by deep imaging is shown in FIG. 5. The problem of displaying the deep image 70 using the viewing screen 34 having a 4:3 aspect ratio is similar to, but the reverse of, the problem of displaying relatively wide images using the viewing screen 34. More specifically, since the image 70 is substantially taller than it is wide, a substantial portion of the viewing screen 34 is unused. Furthermore, it may be difficult to see fine anatomical details in the image 70. These details can be displayed with greater resolution (i.e., using more pixels) and with a larger size by increasing the scale of the image 70, but doing so would cut off the upper and lower ends of the image 70. Thus, viewing screens 34 used with conventional ultrasound imaging systems are less than optimum for displaying both relatively wide images and relatively narrow images. In both cases, substantial areas of the viewing screen 34 are unused, thus reducing the number of pixels of the screen 34 used to display the image.

It would be desirable to make the screen 34 wider. However, given the 4:3 aspect ratio of the screen 34, doing so would proportionately increase the height of the screen 34, thus also making it necessary for the height of the monitor 30 to be increased. Yet, increasing the height of the monitor 30 would make the imaging system quite bulky and eliminate the desirable low-profile appearance of the system 10.

SUMMARY OF THE INVENTION

An ultrasound imaging system for optimally viewing ultrasound images includes a system chassis, an ultrasound transducer coupled to the system chassis, and a display monitor coupled to the system chassis. The display monitor has a viewing screen with an aspect ratio that is substantially greater than 4:3, such as an aspect ratio of 16:9. As a result, certain types of images having a wide aspect ratio, such as panoramic or peripheral images, can be shown with greater size and resolution without cutting off end portions of the image. Furthermore, side-by-side ultrasound images can more optimally be displayed, and Doppler scanned images can be displayed as side-by-side images. The display monitor is preferably mounted on a rotatable base. If the image is wider than it is tall, the display monitor may be rotated to a position in which the aspect ratio of the viewing screen is substantially greater than 4:3. If the image is taller than it is wide, the display monitor may be rotated to a position in which the aspect ratio of the viewing screen is substantially less than 3:4. The display monitor is preferably mounted on top of the system chassis, and the system chassis is preferably placed on a wheeled cart.

DETAILED DESCRIPTION OF THE INVENTION

Figure 6:
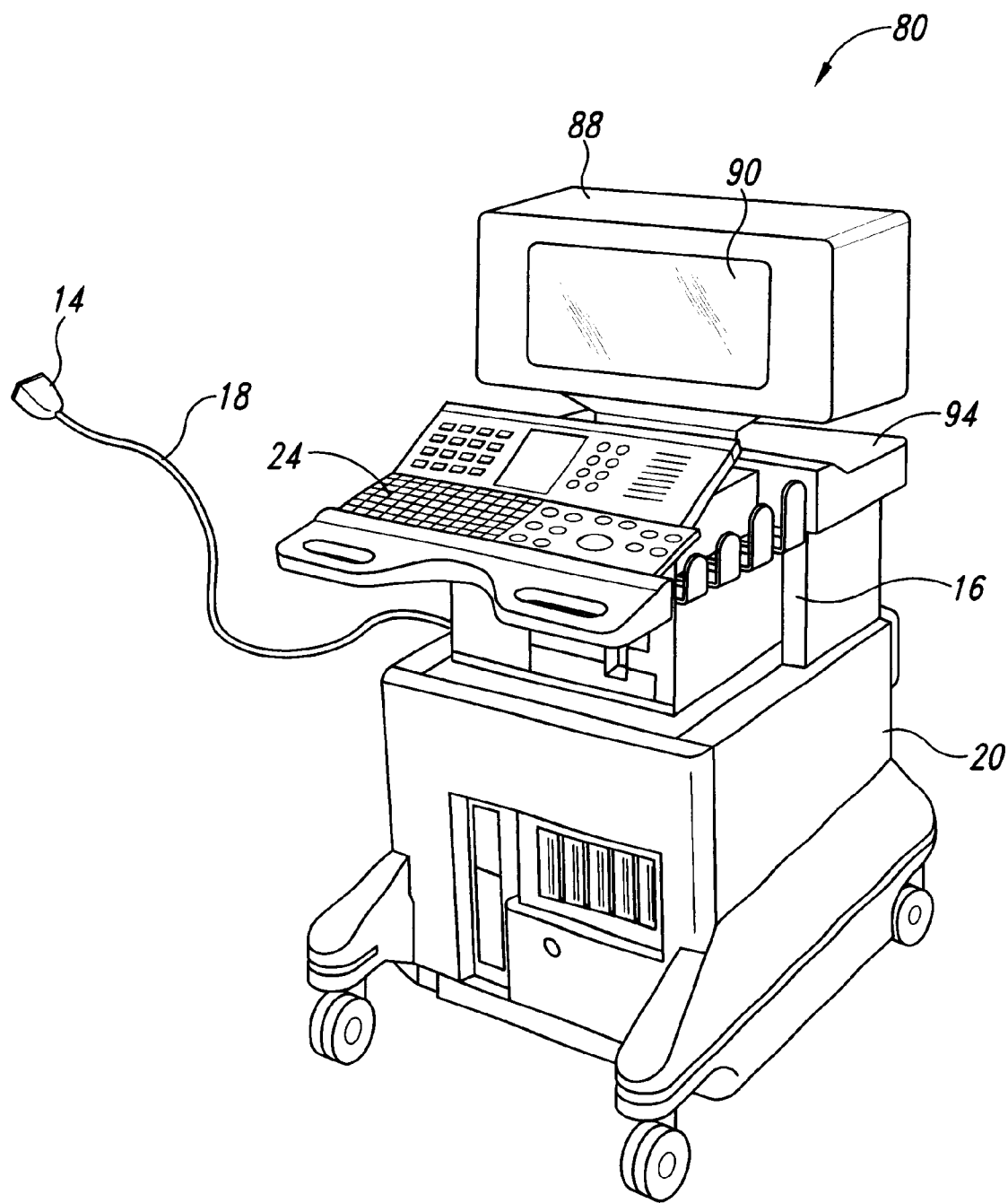
FIG. 6 is an isometric view of a diagnostic ultrasound imaging system according to one embodiment of the invention.

One embodiment of an ultrasound imaging system 80 in accordance with the invention is shown in FIG. 6. The ultrasound imaging system 80 uses most of the same components as the imaging system 10 of FIG. 1. Therefore, in the interest of brevity, these components have been provided with the same reference numerals and an explanation of them will not be repeated. The imaging system 80 differs from the imaging system 10 of FIG. 1 in the use of a display monitor 88 having a viewing screen 90 with a relatively wide aspect ratio. In fact, the aspect ratio of the viewing screen 90 is preferably 16:9 or greater. The display monitor 88 may be, for example, a raster scan display, such as a conventional cathode ray tube ("CRT") display or a projection display, a matrix addressable display, such as a liquid crystal display ("LCD") or a field emission display ("FED"), or some other type of display. The display monitor 88 is preferably mounted on a stand 94 that is, in turn, placed on the upper surface of the system chassis 16. Because of the high aspect ratio of the viewing screen 90, it is able to show images with greater horizontal size without increasing the vertical profile of the imaging system 80. As a result, the low profile of the system 80 is preserved. The display monitor 88 is preferably rotatable with respect to the stand 94 so that it can be rotated to a position in which the viewing screen 90 is relatively wide or to a position in which the viewing screen 90 is relatively tall. Conventional monitors having a 4:3 aspect ratio that are rotatable on a stand are well known and are commercially available.

Figure 2:
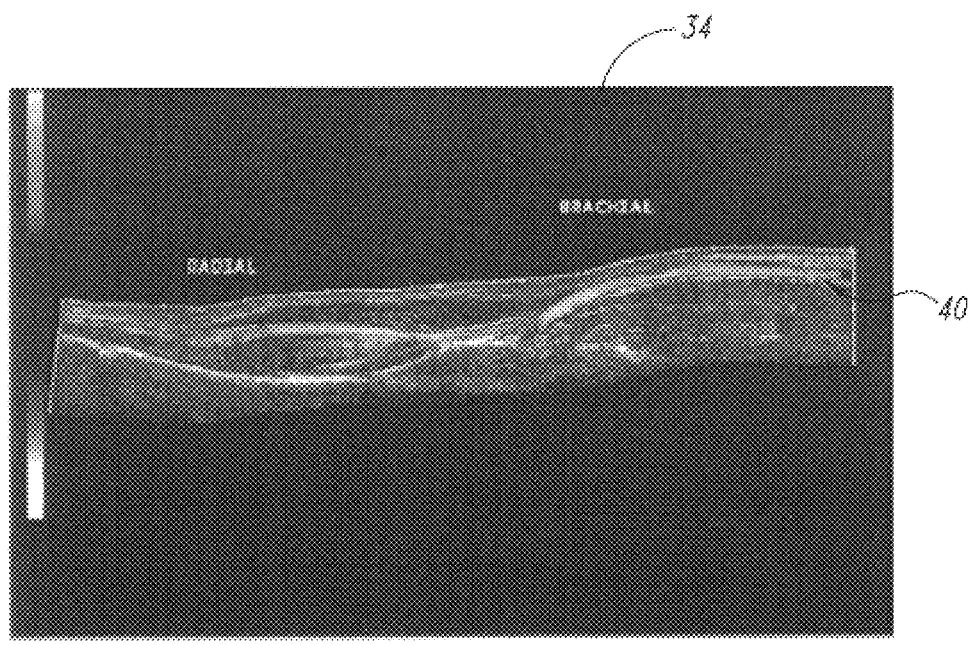
FIG. 2 is a screen display showing a panoramic ultrasound image.
Figure 7:
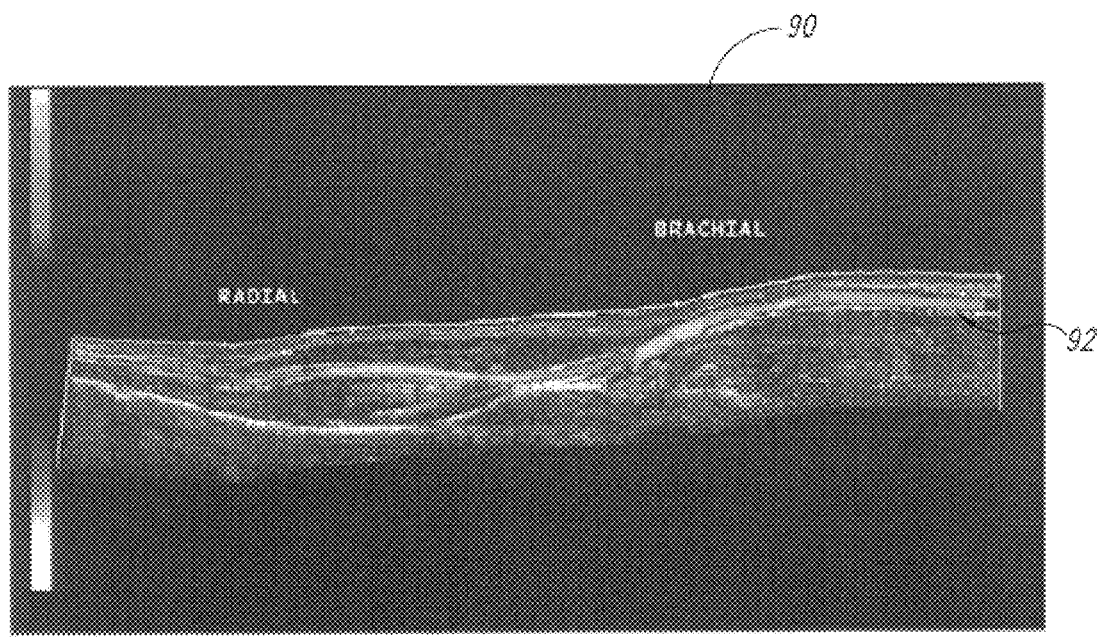
FIG. 7 is a screen display showing a panoramic image obtained using the system shown in FIG. 6.

The advantages of the display monitor 88 used in the imaging system 80 of FIG. 6 can be seen by examining ultrasound images displayed on the viewing screen 90. For example, as shown in FIG. 7, a panoramic image 92 of the same arm shown in the panoramic image 40 of FIG. 2 shows the anatomical features with significantly greater size and resolution, since it uses more pixels to display the image, and still includes the entire length of the image 40 shown in FIG. 2. The advantages of using the ultrasound imaging system 80 with the wide aspect ratio display monitor 88 can also be obtained when using the system 80 for shallow depth or peripheral scanning, which, as explained previously, also produces images that are substantially wider than they are tall.

Figure 3:
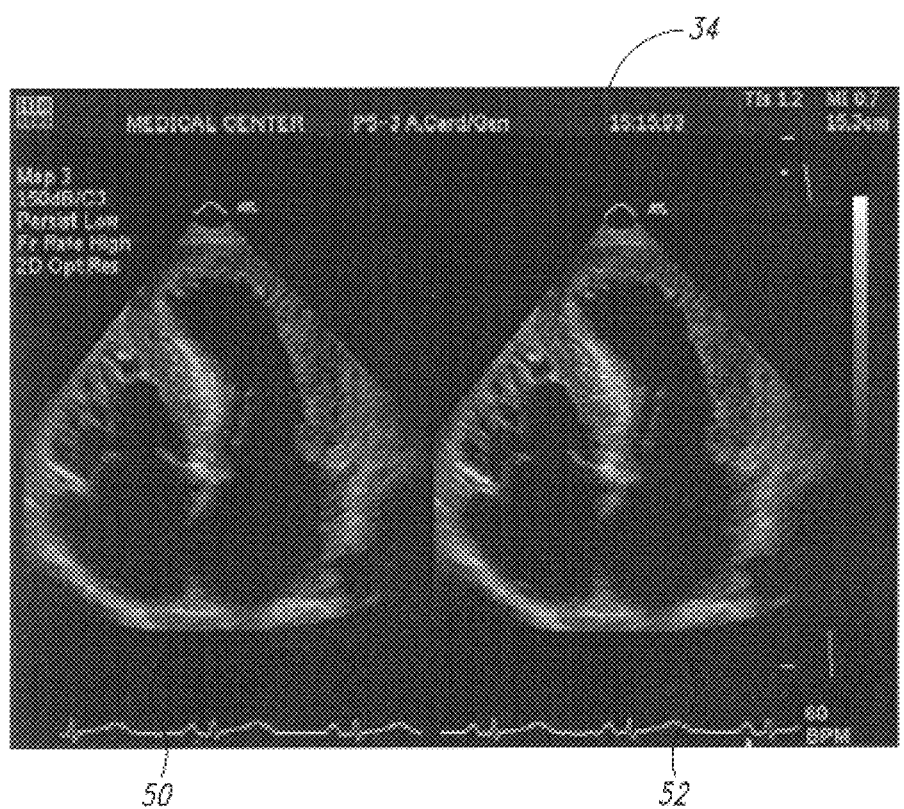
FIG. 3 is a screen display showing side-by-side images obtained using the prior art system of FIG. 1.
Figure 8:
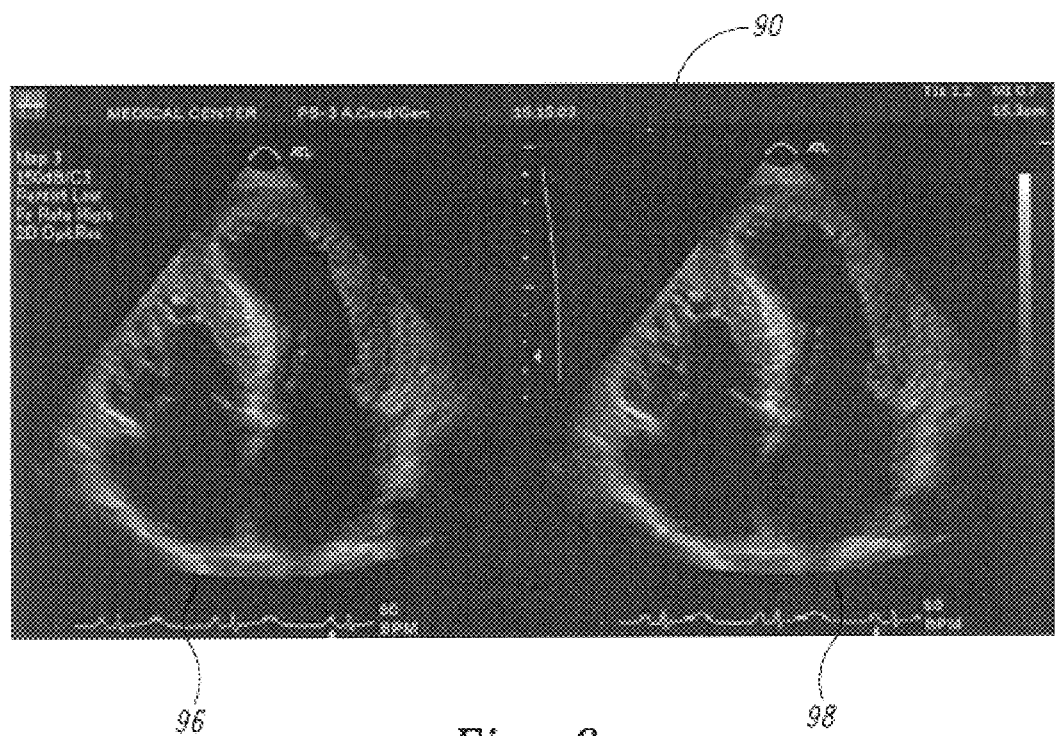
FIG. 8 is a screen display showing a side-by-side image obtained using the system shown in FIG. 6.

By way of further comparison, FIG. 8 shows the viewing screen 90 when the system 80 is used for side-by-side imaging. The left half of the screen 90 is used to display an ultrasound image 96, and the right half of the screen 90 is used to display a second image 98. The image 98 may be, for example, another ultrasound image as is often used in echocardiography, a magnetic resonance image, an x-ray, a nuclear image, an image obtained by CT scanning, an angiograph, or some other image. Alternatively, patient data or other text may be displayed on one side of the screen 90. It can be seen from FIG. 8 that each half of the screen on which the images 96, 98 are displayed has a horizontal dimension that is not substantially smaller than its vertical dimension. In fact, the aspect ratio of the left half of the screen on which the ultrasound image 96 is displayed has an aspect ratio of 8:9, which is almost square. In contrast, the left half of the screen on which the ultrasound image 50 is displayed in FIG. 3 using the prior art system 10 has a substantially greater vertical dimension than a horizontal dimension, i.e., a vertical dimension that is 50% greater than its horizontal dimension.

Figure 4:
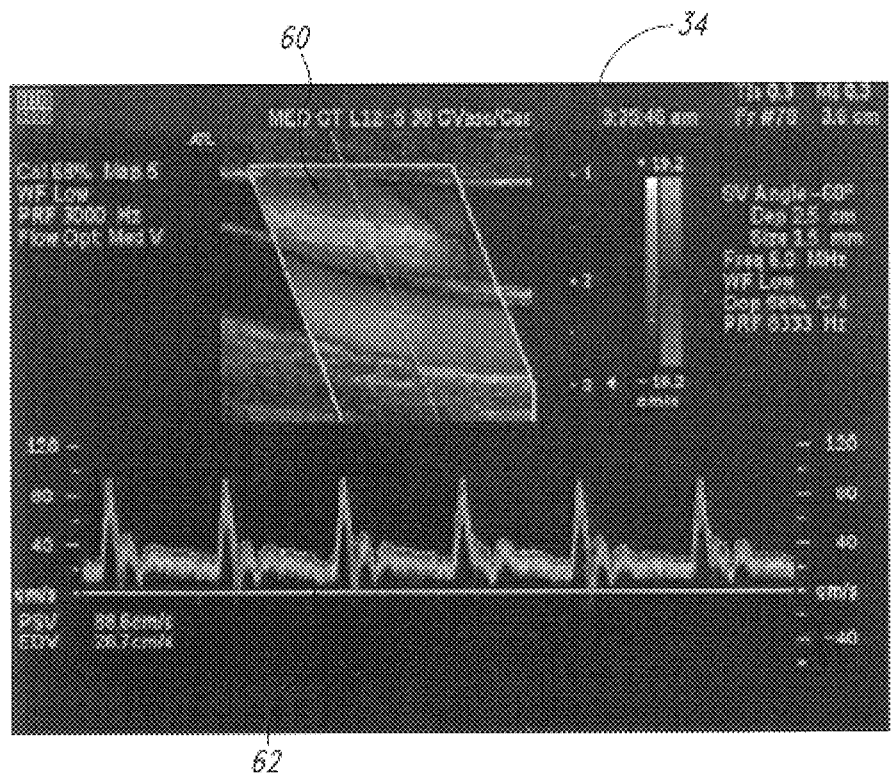
FIG. 4 is a screen display showing an image obtained using the prior art system of FIG. 1 for Doppler scanning.
Figure 9:
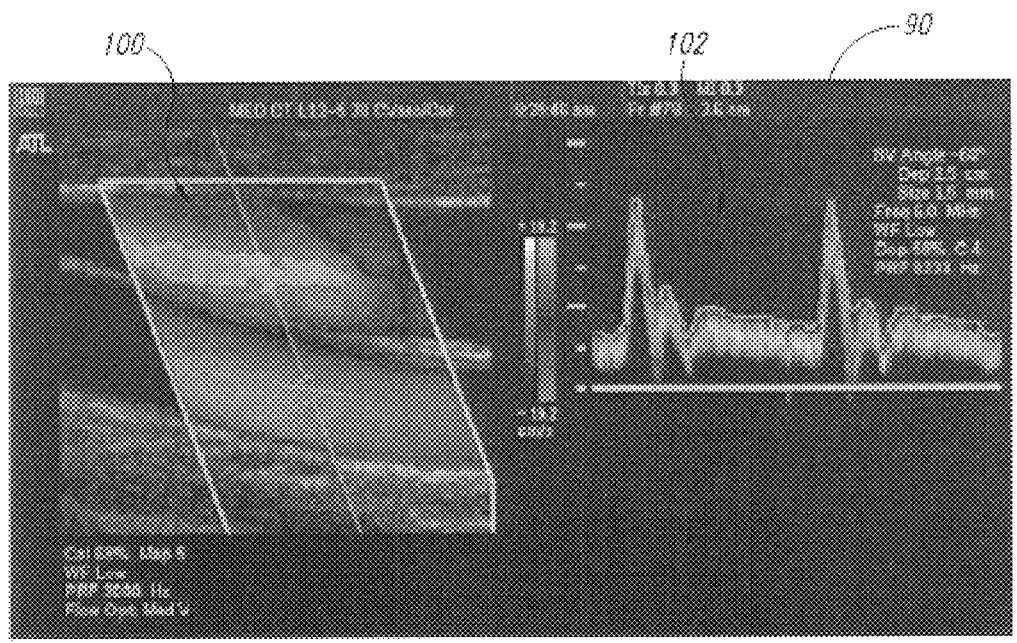
FIG. 9 is a screen display showing an image obtained using the system shown in FIG. 6 for Doppler scanning.

The advantage of using a display having a wider aspect ratio viewing screen 90 is also apparent from an image obtained by Doppler scanning, which is shown in FIG. 9. When the system 80 is used for Doppler scanning, the viewing screen 90 displays an ultrasound image 100 on the left-hand side of the screen 90. Because of the greater width of the screen 90, a scrolling velocity graph 102 can be displayed on the right hand side of the screen 90, thereby allowing the ultrasound image 100 to be displayed on the full height of the screen 90. As a result, the anatomical features in the image 100 can be shown with a larger scale, thus making them more easily visible. In contrast, the prior art Doppler scanned image shown in FIG. 4 usually positions the scrolling velocity graph 62 below the image 60 since there is insufficient room on the screen 34 to position the scrolling velocity graph 62 to the right of the image 60. As a result, the anatomical features in the image 60 are significantly smaller than the display of those same features in the image 100 of FIG. 9.

Figure 5:
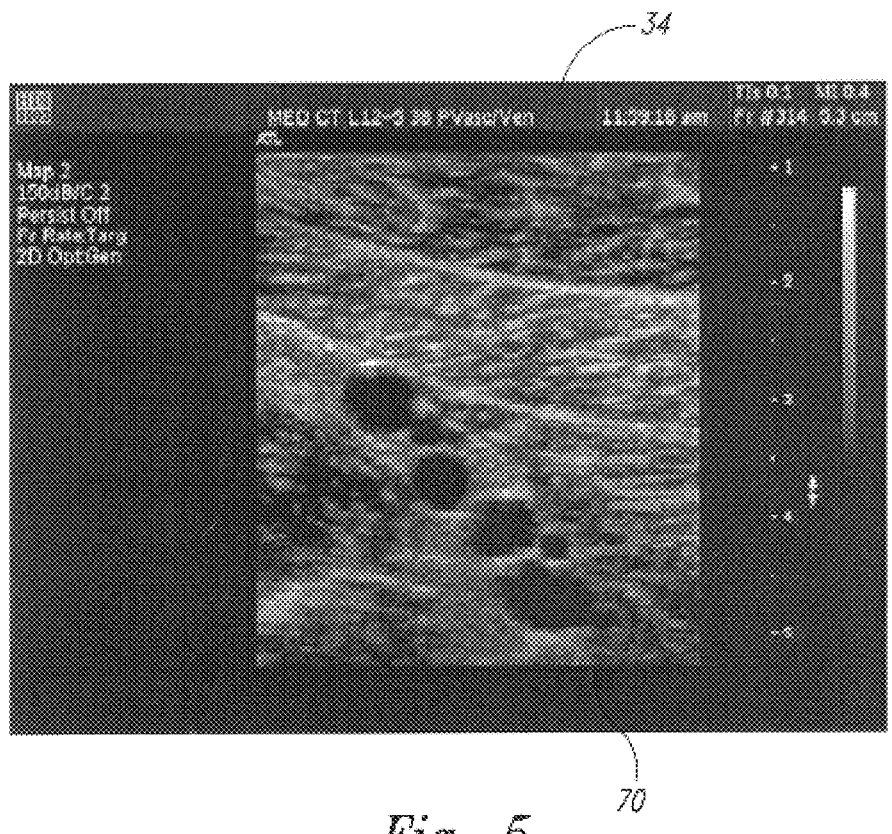
FIG. 5 is a screen display showing an image obtained using the prior art system of FIG. 1 for deep imaging.
Figure 10:
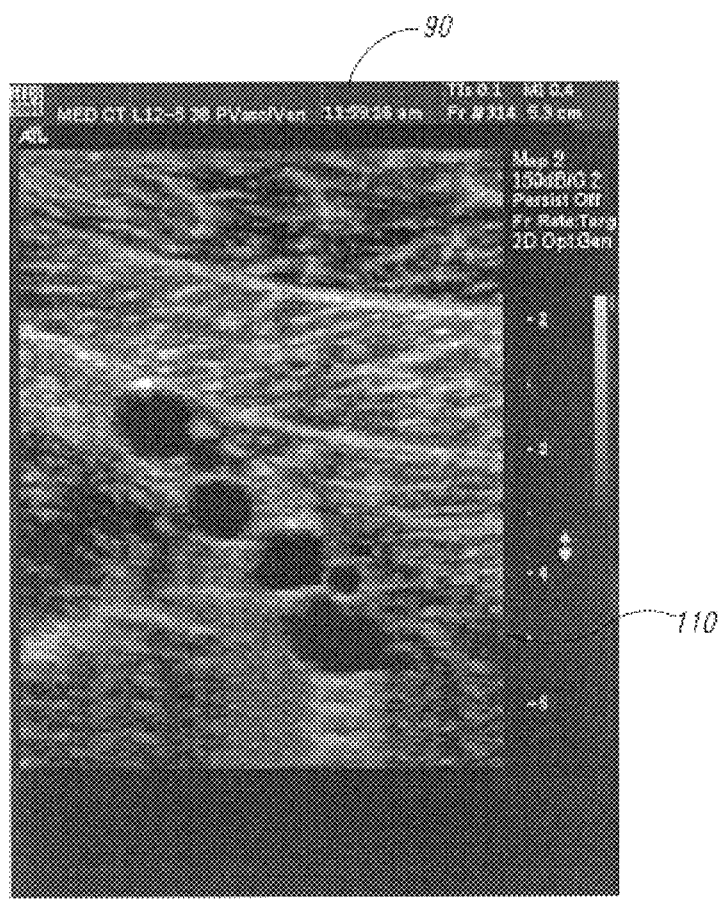
FIG. 10 is a screen display showing a panoramic image obtained using the system shown in FIG. 6 for deep imaging.

The versatility of the display monitor 88 used in the system 80 is illustrated by the use of the system 80 for deep imaging, as shown in FIG. 10. For deep imaging, the monitor 88 is rotated on the stand 94 so that the viewing screen 90 now has an aspect ratio of 9:16. As a result, a deep tissue image 110 uses a substantially greater portion of the screen 90 compared to the deep tissue image 70 shown in FIG. 5. The anatomical details in the image 110 are thus substantially larger than those same details in the image 70 shown in FIG. 5.

Figure 1:
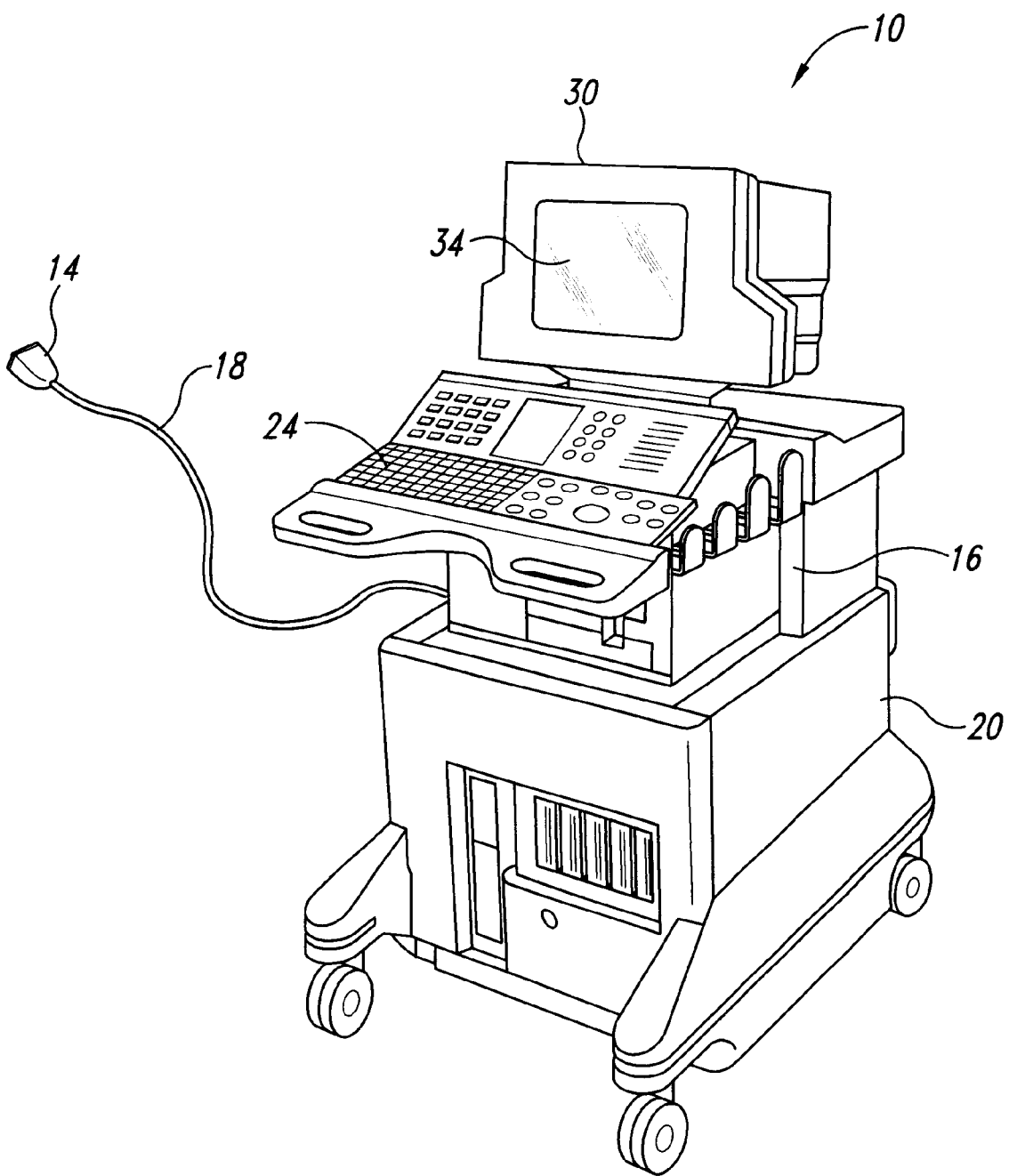
FIG. 1 is an isometric view of a typical prior art diagnostic ultrasound imaging system.

There are also a large number of other imaging applications that can be displayed using the system 80 of FIG. 6 more advantageously than using the prior art system 10 of FIG. 1. For example, images obtained by spatial compounding are often significantly wider than they are tall. Additionally, three-dimensional data obtained by manipulating the ultrasound transducer 14 may also result in an image that is substantially wider than it is tall. Other presently existing or future developed examples will be apparent to one skilled in the art.

From the foregoing it will be appreciated that, although specific embodiments of the invention have been described herein for purposes of illustration, various modifications may be made without deviating from the spirit and scope of the invention. For example, although the exemplary system 80 uses a display monitor 88 having a viewing screen 90 with an aspect ratio of 16:9 it will be understood that different aspect ratios may be used as long as the viewing screen has an aspect ratio substantially greater than 4:3. Moreover, although desirable, it is not necessary that the display monitor 88 be rotatable in its stand 94, although the display monitor 88 would then be unable to display the deep images with the same advantages as explained above with reference to FIG. 10. Accordingly, the invention is not limited except as by the appended claims.

What is claimed is:

1. An ultrasound imaging system, comprising:
   a system chassis;
   an ultrasound transducer coupled to the system chassis; and
   a display monitor coupled to the system chassis, the display monitor having a viewing screen with an aspect ratio that is substantially greater than 4:3.

2. The ultrasound imaging system of claim 1, wherein the display monitor comprises a display monitor having a viewing screen with an aspect ratio of 16:9.

3. The ultrasound imaging system of claim 1 further comprising a base on which the display monitor is mounted, the display monitor being rotatable on the base over an angle of 90 degrees so that rotation of the display monitor transforms the aspect ratio of the viewing screen to a thin aspect ratio.

4. The ultrasound imaging system of claim 1 wherein the display monitor is positioned on an upper surface of the system chassis.

5. The ultrasound imaging system of claim 4, wherein the system chassis is positioned on a wheeled cart, and wherein the display monitor has a width that is less than a width of the cart.

6. The ultrasound imaging system of claim 1 wherein the display monitor comprises a raster scan display.

7. The ultrasound imaging system of claim 6 wherein the raster scan display comprises a cathode ray tube display.

8. The ultrasound imaging system of claim 1 wherein the display monitor comprises a matrix addressable display.

9. The ultrasound imaging system of claim 8 wherein the matrix addressable display comprises a liquid crystal display.

10. The ultrasound imaging system of claim 8 wherein the matrix addressable display comprises a field emission display.

11. A method of displaying a panoramic ultrasound image, comprising:
    providing an ultrasound imaging system including a display monitor having a viewing screen with an aspect ratio that is substantially greater than 4:3;
    obtaining data corresponding to a panoramic image that is substantially wider than it is tall; and
    displaying the panoramic image on the viewing screen with the width of the panoramic image extending along the width of the viewing screen.

12. The method of claim 11 wherein the viewing screen of the display monitor has an aspect ratio of 16:9.

13. A method of displaying a peripheral ultrasound image, comprising:
    providing an ultrasound imaging system including a display monitor having a viewing screen with an aspect ratio that is substantially greater than 4:3;
    obtaining data corresponding to a peripheral image that is substantially wider than it is tall; and
    displaying the peripheral image on the viewing screen with the width of the peripheral image extending along the width of the viewing screen.

14. The method of claim 13 wherein the viewing screen of the display monitor has an aspect ratio of 16:9.

15. A method of displaying a side-by-side ultrasound image, comprising:
    providing an ultrasound imaging system including a display monitor having a viewing screen with an aspect ratio that is substantially greater than 4:3;
    obtaining data corresponding to an ultrasound image;
    obtaining data corresponding to a second image; and
    displaying the ultrasound image on one side of the viewing screen using substantially the full height of the viewing screen; and
    displaying the second image on another side of the viewing screen.

16. The method of claim 15 wherein the viewing screen of the display monitor has an aspect ratio of 16:9.

17. The method of claim 15 wherein the second image comprises textual data relating to a person from whom the ultrasound image was obtained.

18. The method of claim 15 wherein the second image comprises a diagnostic image of one of the imaging modalities of X-ray, CT, magnetic resonance, and nuclear.

19. The method of claim 15 wherein the second image comprises an angiograph.

20. The method of claim 15 wherein the ultrasound image comprises an image of a blood vessel, and wherein the second image comprises a spectral graph.

21. A method of optimally displaying an ultrasound image that may be either substantially wider than it is tall or substantially taller than it is wide, the method comprising:
    providing an ultrasound imaging system including a display monitor that is rotatable by 90 degrees, the display monitor having a viewing screen with an aspect ratio that is substantially greater than 4:3 when the display is rotated to a first position and is substantially less than 4:3 when the display is rotated to a second position;

obtaining data corresponding to an ultrasound image;

determining the aspect ratio of the image;

if the image can be displayed with greater resolution in a display format which is wider than it is tall, rotating the display monitor to the first position;

if the image can be displayed with greater resolution in a display format which is taller than it is wide, rotating the display monitor to the second position; and displaying the ultrasound image on the viewing screen of the display monitor.

22. The method of claim 21 wherein viewing screen of the display monitor has an aspect ratio of 16:9 when the display monitor is rotated to the first position and an aspect ratio of 9:16 when the display monitor is rotated to the second position.

23. The method of claim 21 wherein the ultrasound image comprises a deep image, and wherein the display monitor is rotated to the second position.

24. The method of claim 21 wherein the ultrasound image comprises a peripheral image, and wherein the display monitor is rotated to the first position.

25. The method of claim 21 wherein the ultrasound image comprises a panoramic image, and wherein the display monitor is rotated to the first position.

26. The method of claim 21 wherein the ultrasound image comprises a graphical display, and wherein the display monitor is rotated to the first position.

27. The method of claim 21 wherein the display monitor comprises a matrix addressable display.

28. The method of claim 27 wherein the matrix addressable display comprises a liquid crystal display.

29. The method of claim 27 wherein the matrix addressable display comprises a field emission display.

* * * * *